United States Patent
Connors, III et al.

(10) Patent No.: US 7,595,082 B2
(45) Date of Patent: Sep. 29, 2009

(54) WIRE GUIDE

(75) Inventors: John J. Connors, III, Tampa, FL (US);
Kurt J. Tekulve, Elletsville, IN (US);
Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 1153 days.

(21) Appl. No.: 10/813,423

(22) Filed: Mar. 30, 2004

(65) Prior Publication Data

US 2004/0185179 A1    Sep. 23, 2004

Related U.S. Application Data

(62) Division of application No. 10/227,048, filed on Aug. 23, 2002, now Pat. No. 7,001,345.

(51) Int. Cl.
*B05D 3/12* (2006.01)
*A61M 25/09* (2006.01)
*A61M 31/00* (2006.01)

(52) U.S. Cl. .................. 427/2.28; 427/2.1; 427/2.24; 427/2.25; 427/331; 427/355; 600/434; 600/585; 604/95.03; 604/523; 604/525; 604/526

(58) Field of Classification Search .................. 427/2.1, 427/2.24, 2.25, 2.28, 331, 355, 356, 358, 427/368; 600/434, 585; 604/95.03, 523, 604/525

See application file for complete search history.

(56) References Cited

U.S. PATENT DOCUMENTS 4,884,579 A    12/1989  Engelson
5,069,226 A    12/1991  Yamauchi et al.

(Continued)

FOREIGN PATENT DOCUMENTS

EP    0 769 306 A2    4/1997
JP    09094298         4/1997

OTHER PUBLICATIONS

"Spray painting tips and tutorial," http://alsnetbiz.com/homeimprovement/spraypainting.html. Apr. 2, 2002.*

(Continued)

*Primary Examiner*—Timothy H Meeks
*Assistant Examiner*—Cachet I Sellman
(74) *Attorney, Agent, or Firm*—Brinks Hofer Gilson & Lione

(57) ABSTRACT

A wire guide includes a mandrel that has a proximal portion and a distal portion. A first coating with a low coefficient of friction is disposed on the proximal portion of the mandrel. A second coating is disposed on the distal portion of the mandrel, where the second coating provides a sub-structure. A third coating is disposed on the second coating, where the third coating comprises a surface that allows for easy maneuverability of the wire guide. The first coating on the proximal portion provides enough lubricity to keep the wire guide from becoming bound or stuck in a catheter or medical device while still allowing a user to have a good grip of the wire guide. The second coating on the distal portion provides lubricity for the wire guide, which allows the user to easily maneuver the wire guide through a vascular anatomy.

5 Claims, 2 Drawing Sheets

U.S. PATENT DOCUMENTS

| | | | |
|---|---|---|---|
| 5,129,890 | A | 7/1992 | Bates et al. |
| 5,159,861 | A | 11/1992 | Anderson |
| 5,325,746 | A | 7/1994 | Anderson |
| 5,443,455 | A * | 8/1995 | Hergenrother et al. ...... 428/380 |
| 5,452,726 | A | 9/1995 | Burmeister et al. |
| 5,749,837 | A | 5/1998 | Palermo et al. |
| 5,756,144 | A | 5/1998 | Wolff et al. |
| 5,772,609 | A | 6/1998 | Nguyen et al. |
| 6,139,510 | A | 10/2000 | Palermo |
| 6,340,441 | B1 | 1/2002 | Meyer et al. |
| 6,409,682 | B1 * | 6/2002 | Burmeister et al. ......... 600/585 |
| 6,494,894 | B2 | 12/2002 | Mirarchi |
| 6,652,472 | B2 * | 11/2003 | Jafari et al. ................. 600/585 |
| 2003/0023190 | A1 * | 1/2003 | Cox ........................... 600/585 |
| 2003/0087024 | A1 * | 5/2003 | Flanagan ................... 427/2.24 |

OTHER PUBLICATIONS

Nurdin, N., Lubricating Coating On Polyurethane Catheter, http://www.unige.ch/gap-b/projet/nathalie/catheter.html.

MatWeb, Chemical Properties Overview For PTFE, http://www.matweb.com/search/SpecificMaterial.asp?bassnum=O1900.

* cited by examiner

WIRE GUIDE

CROSS-REFERENCE TO RELATED APPLICATIONS

This patent application is a divisional of U.S. patent application Ser. No. 10/227,048, which was filed on Aug. 23, 2002 now U.S. Pat. No. 7,001,345.

BACKGROUND OF THE INVENTION

Generally, a wire guide can be used for the placement of a catheter into a vascular system. A wire guide has a proximal end that is held by a physician and a distal end that is inserted into the vascular system. A physician may insert a needle with the wire guide into an artery, vein or other vessel. The wire guide is introduced through the needle into the vessel. Next, the needle is withdrawn over the wire guide, then a catheter or another medical device is placed over the wire. This medical device and the wire guide are maneuvered together to a part of the vascular anatomy at which the physician is performing an interventional or diagnostic procedure.

These wire guides include low coefficient of friction coatings so the catheters can be advanced over them freely and they can be passed into the vascular anatomy easily. These coatings are typically made of Polytetraflouroethylene (Teflon), and hydrophilics (polyvinylpirilidone). The Teflon coating is usually effective for allowing free movement of the catheter over the wire guide, but not effective for allowing the wire guide to pass freely into the vascular anatomy. The hydrophilic coating is effective for allowing the wire guide to advance into the vascular anatomy and allowing free movement of the catheter over the wire, however, the hydrophilic coating is too slippery to allow the physician to grip and maneuver the wire guide.

One of the problems with such wire guides is that they do not provide a good feel for the physician, which makes it difficult to determine if the wire guide is advancing through the vascular anatomy or if the physician's fingers are slipping along the proximal end. Some methods or devices have attempted to provide the appropriate feel and control of the wire guides. One device is a pin vise type that securely clamps to the proximal end of the wire. This device is described in U.S. Pat. No. 5,325,746. This device acts as a handle for the wire guide, which allows a physician to easily manipulate the wire guide. Since this device usually must be positioned and repositioned during an invasive procedure, a physician using it may find it difficult and/or cumbersome to operate. Another attempted solution involves coating the distal end of the wire guide with a hydrophilic layer leaving the proximal end uncoated to prevent the proximal end from being slippery. This approach allows the physician to feel and manipulate the wire guide in the usual manner. Since the proximal end is uncoated, however, it can stick or bind in the lumen of the catheter or super-selective catheter. A super-selective catheter is a specially made medical device used to enter vessels that are inaccessible by normal catheters. More specifically, the proximal end of the wire guide can bind to the lumen of superselective catheters made of Nylon, making it difficult to use the wire guide with the catheter. Therefore, there is a need for an apparatus and a method that enables a user to retain a good grip on the wire guide while providing enough lubricity to allow the wire guide to function well.

BRIEF SUMMARY OF THE INVENTION

The present invention has been accomplished in view of the above-mentioned technical background, and it is an object of the present invention to provide a lubricious wire guide having improved handling ability. In a first preferred embodiment, a wire guide includes a mandrel that has a proximal portion and a distal portion. A first coating with a low coefficient of friction is disposed on the proximal portion of the mandrel. A second coating is disposed on the distal portion of the mandrel, where the second coating provides a sub-structure. A third coating is disposed on the second coating, where the third coating comprises a surface that allows for easy maneuverability of the wire guide. In another preferred embodiment, a method for making a wire guide is disclosed. A mandrel having a proximal portion and a distal portion is provided. A first coating with a low coefficient friction is applied over the mandrel, where the mandrel has a proximal portion and a distal portion. The first coating is removed from the distal portion of the mandrel. A coil is connected to the distal portion of the mandrel. A second coating is applied over the distal portion of the mandrel, where the second coating provides a good sub-structure. A third coating is applied over the first coating, where the third coating comprises a surface that allows for easy maneuverability of the wire guide.

BRIEF DESCRIPTION OF THE DRAWINGS

These and other advantages of the present invention will become more apparent as the following description is read in conjunction with the accompanying drawings, wherein.

DETAILED DESCRIPTION OF THE INVENTION

The presently preferred embodiments of the invention are described with references to the drawings, where like components are identified with the same numerals. The descriptions of the preferred embodiments are exemplary and are not intended to limit the scope of the invention.

Figure 1:
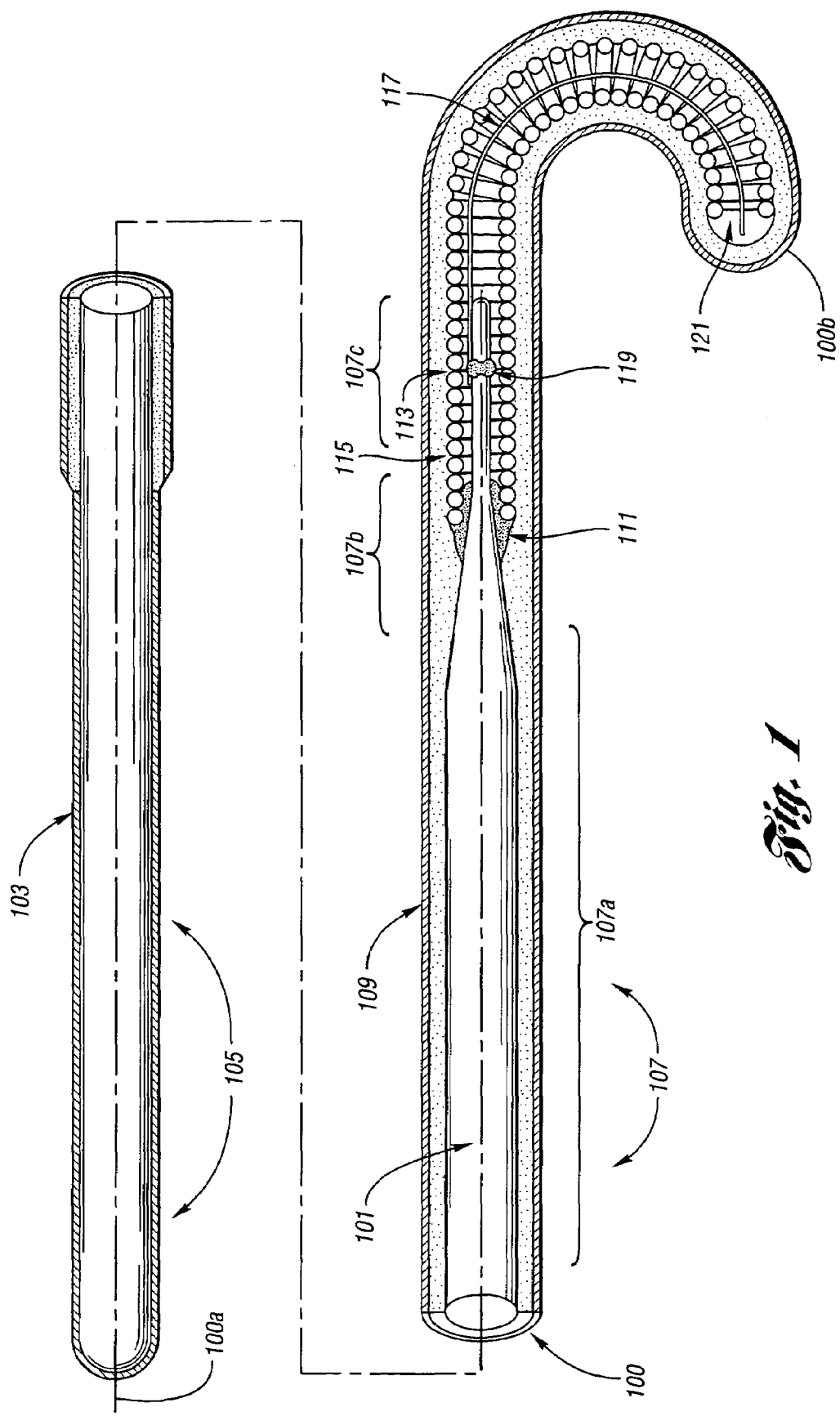
FIG. 1 is an illustration of a wire guide in accordance with an embodiment of the invention.

FIG. 1 is an illustration of a wire guide in accordance with a preferred embodiment of the invention. Wire guide 100 includes a mandrel or elongated central core 101 made of a Nitinol material, although it can be made from many other materials. Mandrel 101 should be made of a flexible, elastic or bendable material that is flexible enough to traverse the vessels or arteries. Preferably, the mandrel is made of a thin spring temper stainless steel material. Mandrel 101 can be made of other materials that have properties similar to stainless steel and Nitinol, such as the properties of being kink resistant, being able to withstand sterilization (heat and moisture) and being non toxic etc. Preferably, the Nitinol wire core is made of about 50/50 mix of Nickel and Titanium in a super-elastic condition at or below a room temperature of 0 degrees Celsius.

The length of the wire guide may range from about 40 centimeters (cm) to about 480 centimeters (cm). An outside diameter of the wire guide 100 may range from about 0.008 inches to about 0.05 inches. The outside diameter of the wire guide 100 is determined by a diameter of the mandrel 101 and a thickness of any coating that encloses the mandrel 101 such as coatings (first) 103, 109 (third), 113 (second). Preferably, the outside diameter of the wire guide 100 is in the range of about 0.010 inches to about 0.038 inches. In the preferred embodiment, the diameter of the mandrel 101 is the range of about 0.008 inches to about 0.050 inches. The thickness of coatings 103, 109 and 113 are discussed below.

Wire guide 100 has a generally cylindrical shape and includes a straight shaped proximal end 100a and a j-shaped distal end 100b. The j-shaped distal end 100b has a radius of curvature in a range of about 1.0 millimeters to about 9 millimeters (mm), which are popular radius ranges and make the j-shaped distal end 100b of the wire guide 100 less traumatic to the vessel wall. Preferably, the radius of the j-shaped distal end 100b is about 3 mm. When the j-shaped distal end 100b is used it is first straightened so it can be inserted into the vessel. Once the j-shaped distal end 100b is in the vessel it transforms and presents a smooth surface to the vessel wall wherever the wire guide 100 contacts the vessel wall as it is being advanced through the vascular system. In alternative preferred embodiments, the j-shaped distal end 100b may also have other shapes, such as may be useful for negotiation movement through the particular vascular anatomy. Also, in alternative preferred embodiments, the proximal end 100a may also have a rectangular shape or any other shape designed to provide a good grip that helps a physician maneuver the wire guide 100 through the vascular anatomy.

Preferably, the mandrel 101 has a substantially uniform diameter at its proximal portion 105 and a tapered diameter at its distal portion 107, as shown by 107b. The proximal portion 105 may have a length ranging from about 20 cm to about 300 cm. In the preferred embodiment, proximal portion 105 has a length that is about one half of the total length of the wire guide 100. This preferred proximal portion 105 may be covered by the (first) coating 103 that includes any material, such as a polymer, that has a surface exhibiting a low coefficient of friction. Preferably, the polymer is Teflon.

Coating 103 can also be a high density polyethylene or Nylon, which has a coefficient of friction lower than that that of a bare Nitinol or stainless steel wire. In this case, the coefficient of friction for coating 103 is in relation to stainless steel, which has a coefficient of friction of about 1. The low coefficient of friction for coating 103, preferably, is in a range of about 0.01 to about 0.9.

Most preferably, the low coefficient of friction for coating 103 is in the range of about 0.01 to 0.7. This low coefficient of friction is sufficient to allow the physician to grasp and handle the proximal portion 100a securely, but low enough to slide the wire guide 100 through a catheter. Preferably, the coating 103 is made of a polytetrafluoroethylene (Teflon) material, which has a coefficient of friction of about 0.6. The thickness of the coating 103 on the mandrel 101 ranges from about 0.00002 inches to about 0.080 inches.

Preferably, the thickness of coating 103 on the mandrel 101 ranges from about 0.0002 inches to about 0.020 inches.

Preferably, the distal portion 107 includes an elongated portion 107a, a tapered portion 107b and an un-tapered portion 107c. The length of the elongated portion 107a varies from about 60 to about 70 cm. In the preferred embodiment, the length of the elongated portion 107a is about one half of the total length of the wire guide 100. The tapered portion 107b has a length that varies from about 1 cm to about 30 cm. Preferably, the tapered portion 107b may be about 10 cm long with the distal tip, and the un-tapered portion 107c is about 2 cm long. A first solder joint 119 connects a safety wire 117 to the un-tapered portion 107c. Preferably, the solder joint 119 connects the safety wire 117 to a distal tip of the un-tapered portion 107c. The safety wire 117 extends into a distal tip area 121 of a tip coil 115. The tip coil 115, preferably, encompasses only partially tapered portion 107b, un-tapered portion 107c, safety wire 117 and the first solder joint 119. Many other types of connections can be used in place of the first solder joint 119, such as an adhesive, glue or a connection device. Alternatively, the un-tapered portion 107c may not be soldered or even connected to the safety wire 117. If there is no safety wire 117 soldered to the un-tapered portion 107c and a tip coil 115 that surrounds the un-tapered portion 107c, then the un-tapered portion 107c can be extended and curved to be in contact and connected to with the distal tip area 121.

In another alternative embodiment, there is no first solder joint 119 to connect safety wire 117 to un-tapered portion 107c, which extends to the distal tip area 121; instead, the safety wire 117 is connected to tapered portion 107b by utilization of the second solder joint 111 that extends to the distal tip area 121. In yet another alternative embodiment, there is no safety wire 117 and no first solder joint 119 connected to un-tapered portion 107c; instead, the un-tapered portion 107c length is extended and angled to be in contact and connected to the distal tip area 121.

The tip coil 115 is connected or soldered by a second solder joint 111 to the tapered portion 107b. Preferably, the tip coil 115 is radiopaque and made of platinum, platinum alloy, stainless steel or any other suitable material. Platinum alloy is used because it is dense enough to be seen clearly under an X-ray.

The distal portion 107 is coated or layered with a second coating 113 and a third, hydrophilic coating 109. In an alternative preferred embodiment, the distal portion 107 and/or tip coil 115 may only be coated with coating 109. In another alternative preferred embodiment, the distal portion 107 and/or tip coil 115 may only be coated with coating 113.

Preferably, the coating 113 is made of a polymeric material, such as nylon, polyethylene, polyurethane etc. Coating 113 is made of a polymer material since it is acceptable as a sub-structure for the coating 109 and coating 113 provides a good foundation and bonding material, which supports coating 109. In the preferred embodiment, coating 113 has a range of thickness from about 0.001 inches to about 0.010 inches. In the presently preferred embodiment, the thickness of the coating 113 is about 0.006 inches.

Alternative preferred embodiments of coating 113 can use polymeric material having different thicknesses to stiffen the wire guide 100 or make the wire guide 100 more flexible. In the preferred embodiment, coating 113 is made of a polyurethane material, because it has an attraction to the hydrophilic coating 109, which indicates that the coating 109 will be secured to coating 113. In addition, polyurethane is very flexible and provides for good adhesion to the hydrophilic coating 109. Furthermore, formulations of polyurethane when applied to the mandrel 101 do not detract from the characteristics of the wire guide 100 by changing its flexibility.

Hydrophilic coating 109 has a polished or very slick surface with a coefficient of friction in the range of about 0.01 to 0.1 that allows the wire guide 100 to easily maneuver through the vascular anatomy. The coefficient of friction for hydrophilic coating 109 is lower than the coefficient of friction for coating 103. The hydrophilic coating 109 contains a solvent in its un-cured state that is attracted to the polyurethane, which indicates there is a good bond between the hydrophilic coating 109 and the coating 113. The hydrophilic coating 109 can be made of one of many materials that typically have Polyvinylpirildone (PVP) as the base material. The hydrophilic coating 109 has a range of thickness from about 0.0001 inches to about 0.005 inches. In the preferred embodiment, the thickness of coating 109 is about 0.001 inches.

Preferably, the tip coil 115 is also coated with the coating 113 and hydrophilic coating 109 as it forms the j-shaped distal end 100b. The tip coil 115 can be coated with a combination of coating 113 and coating 109, where the combination thickness is about 0.001 inches to about 0.010 inches. Preferably, this combination of coating 113 and 109 is about 0.003 inches. Alternatively, the tip coil 115 may not be coated with the coating 113 and the coating 109.

Figure 2:
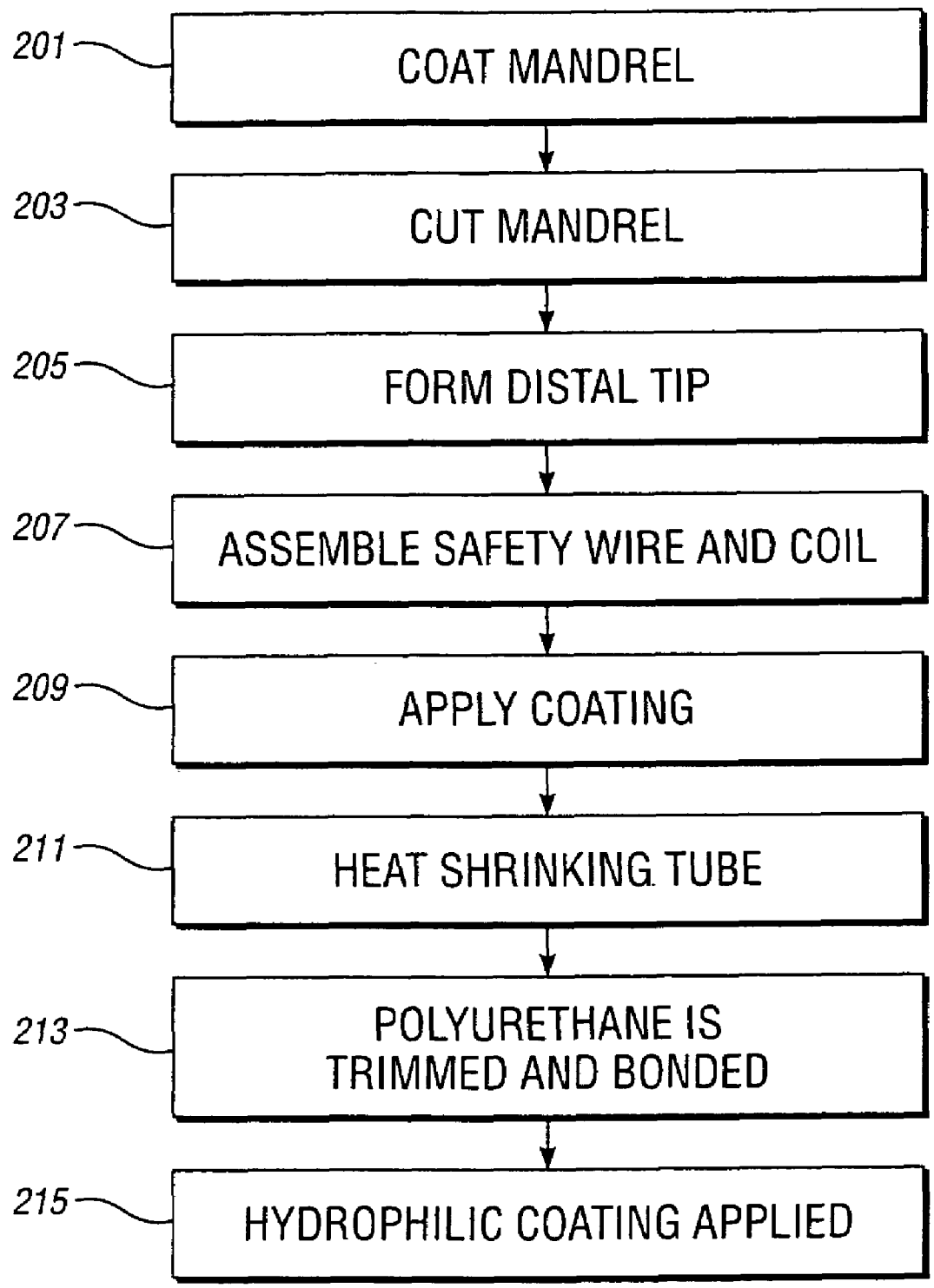
FIG. 2 is a flow chart of a method of manufacturing a wire guide in accordance with the invention.

FIG. 2 is a flow chart of a method of manufacturing a wire guide in accordance with this invention. At 201, coating 103 is applied over the un-tapered Nitinol wire or mandrel 101. Preferably, coating 103 fully coats the proximal portion 105 and the distal portion 107 (not shown) of the wire guide 100. The coating 103 may be positioned over or applied over mandrel 101 by dipping, spraying, over-extruding or by using any other coating method. Over-extruding involves melting coating 103, and passing the Nitinol wire through an extruder so that the melted coating 103 envelops the wire. Alternatively, the coating 103 is applied over mandrel 101 by spraying or die wiping.

At 203, the coated Nitinol wire 101 is cut into the desired length, depending on the length of the desired finished wire guide 100, ranging from about 40 cm to about 160 cm. Cutting the wire is performed by any method or device. Preferably, the wire is cut by using a standard wire cutter. At 205, the coated wire guide 100 undergoes a centerless grinding process in which a distal tip taper for the wire guide 100 is formed and the coating 103 is removed from the distal portion of the wire guide 100. The grinding process removes the coating 103 approximately 5-140 cm from a distal tip of the wire guide 100 to the start of the proximal end 100a of the wire guide 100 leaving the proximal end 100a coated with coating 103. Preferably, the amount of coating 103 removed from the distal tip of wire guide 100 to the start of the proximal end 100a is in the range of about 20-80% of the length of the wire guide 100. In the preferred embodiment, the coating 103 is removed from about 50% of the length of the wire guide 100. For example, if the length of the wire guide 100 is approximately 150 cm, then about 75 cm of coating 103 is removed from the distal end of the wire guide 100.

At 207, a safety wire 117 is connected to the un-tapered portion 107c. In the preferred embodiment, the safety wire 117 is soldered to the un-tapered portion 107c by utilization of the first solder joint 119. The tip coil 115 is connected to the tapered portion 107b of the wire. Preferably, the tapered portion 107b is soldered to the tip coil 115 by the utilization of the second solder joint 111. Preferably, the tip coil 115 includes the distal tip area 121.

At 209, a thin extruded sleeve of coating 113 is applied over the distal portion 107. Preferably, the coating 113 is made of a polymeric material, such as polyurethane. In the preferred embodiment, a shrink tube is used to make the sleeve of coating 113 conform to the shape of distal portion 107 or mandrel 101 by slipping the shrink tube over the sleeve of coating 113. Preferably, the shrink tube is made of a polymer, such as expanded Polytetrafluoroethylene (ePTFE), Perfluoro (ethylene-propylene) copolymer (FEP), polypropylene and Perfluoalkoxyalkane (PFA).

A shrink percentage of the shrink tube is in the range of about 10% to about 99%. The shrink tube shrinks by using the heating process discussed below. The shrink tube only needs to shrink down to a diameter equal to or smaller than the outside diameter of the wire guide 100. The diameter of the shrink tube before shrinking only needs to be large enough to fit over the coating 113 before shrinking. In the preferred embodiment, the shrink tube has a diameter in the range of about 1/16 of an inch. The length of the shrink tube depends on the length of the wire guide 100 covered with the sleeve of coating 113. In the preferred embodiment, the length of the shrink tube only needs to be slightly longer than the sleeve coating 113, which is about 2 cm to about 5 cm. The shrink tube has a wall thickness in the range of about 0.0001 inches to about 0.008 inches. Preferably, the wall thickness of the shrink tube is in the range of about 0.001 to 0.005 inches range.

When coating 113 is slipped over the distal portion 107 or mandrel 101, a thin wire that has a diameter in the range of about 0.0001 to about 0.009 inches is placed between the shrink tube and the sleeve coating 113. At 211, the combination of the shrink tube, thin wire and sleeve coating 113 is then heated, causing the shrink tube to shrink onto sleeve coating 113. The shrink tube is heated to approximately 250-400 degrees. Preferably, the shrink tube is heated to about 320-350 degrees.

The shrinking of the shrink tube causes the coating 113 to melt and the coating 113 becomes uniformly snug to conform to the shape of the distal portion or mandrel 101. Next, the shrink tube is removed, leaving the coating 113 on the distal portion 107 or mandrel 101. After the shrinking process, one end of the thin wire can be pulled so that it cuts the shrink tube from one end to the other. Once the shrink tube has been slit along its full length, it can be peeled off easily to separate the shrink tube from coating 113. The thin wire is so small that the indentation it makes in the coating 113 during the melting/shrinking process is undetectable.

At 213, an excess of the coating 113 is trimmed and rounded at the j-shaped distal end 100b. Coating 113 may be trimmed and rounded at the j-shaped distal end 100b of the wire guide 100 by any method. Preferably, the excess is trimmed by using a razor blade. The razor blade gives a flat cylindrical shape to the j-shaped distal end 100b of the wire guide 100. The tip of the wire guide 100 is then rounded by hand using a grinder with sandpaper.

At 215, a lubricious layer or coating 109, such as a hydrophilic coating is applied over the coating 113, which covers distal portion 107. This lubricious coating may be applied by spraying, dip coating, over-extruding or by any other means.

As described above, the proximal portion of the wire guide is covered with a material that has a low coefficient of friction. This material is used to provide a good grip for the physician using the wire guide while still providing a surface that will slide freely through the lumen of the catheter or medical device. This material provides an improved proximal portion that assists physicians in maneuvering the wire guide through the vascular system. In addition, the distal portion of the wire guide includes a polymer coating that provides good flexibility for a wire guide and is a good base for adhesion of the hydrophilic coating. The hydrophilic coating is used because it has a very slick surface that allows the wire guide to easily maneuver through the vascular anatomy, which improves the maneuverability of the wire guide through the vascular anatomy.

This combination of coatings on the proximal and distal portions of the wire guide enables the wire guide to be easily maneuvered through the vascular anatomy without becoming bound or stuck in the catheter. In addition, this wire guide provides the physician with a gripping area to maneuver the wire guide accurately and safely.

It is intended that the foregoing detailed description be regarded as illustrative rather than limiting and that it be understood that it is the following claims, including all equivalents, which are intended to define the scope of the invention.

The invention claimed is:

1. A method for making a wire guide comprising:
   providing a mandrel having a proximal portion and a distal portion;
   applying a first coating having a low coefficient friction over the mandrel;

removing the first coating from the distal portion of the mandrel;

connecting a coil to the distal portion mandrel;

applying a second coating over the distal portion of the mandrel, wherein the second coating provides a substructure; and applying a third coating over the second coating, wherein the third coating comprises a surface that allows for easy maneuverability of the wire guide.

2. The method of claim 1 wherein the surface comprises a polished surface.

3. The method of claim 1 wherein removing the first coating from the distal portion of the mandrel further comprises forming a tapered portion on the distal portion of the mandrel.

4. The method of claim 1, wherein the surface allows for the easy maneuverability of the wire guide through a vascular anatomy.

5. A method for making a wire guide comprising:

providing a mandrel having a proximal portion and a distal portion;

applying a first coating having a low coefficient friction over the mandrel;

removing the first coating from the distal portion of the mandrel;

applying a second coating over the distal portion of the mandrel, wherein the second coating provides a substructure;

applying a third coating over the second coating, wherein the third coating comprises a surface that allows for easy maneuverability of the wire guide.

* * * * *

UNITED STATES PATENT AND TRADEMARK OFFICE
CERTIFICATE OF CORRECTION

PATENT NO. : 7,595,082 B2  Page 1 of 1
APPLICATION NO. : 10/813423
DATED : September 29, 2009
INVENTOR(S) : Connors, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1223 days.

Signed and Sealed this

Twenty-eighth Day of September, 2010

David J. Kappos
*Director of the United States Patent and Trademark Office*